United States Patent [19]

Mörmann et al.

[11] 4,211,232
[45] Jul. 8, 1980

[54] MUCOUS MEMBRANE CUTTER FOR MUCOGINGIVAL MEMBRANE SURGERY

[75] Inventors: Werner Mörmann, Zürich, Switzerland; Gerhard Bofinger, Immendingen-Hattingen; Wilfried Wölfie, Bad Dürrheim, both of Fed. Rep. of Germany

[73] Assignee: Aesculap-Werker Aktiengesellschaft, vormals Jetter & Scheerer, Tuttlingen, Fed. Rep. of Germany

[21] Appl. No.: 873,935

[22] Filed: Jan. 31, 1978

[30] Foreign Application Priority Data

Feb. 22, 1977 [DE] Fed. Rep. of Germany ....... 2707523

[51] Int. Cl.$^2$ ............................................. A61B 17/322
[52] U.S. Cl. ................................... 128/305.5; 30/392
[58] Field of Search ............... 128/305.5, 305, 305.1; 30/394, 392

[56] References Cited

U.S. PATENT DOCUMENTS

| | | | |
|---|---|---|---|
| 1,736,246 | 11/1929 | Blair | 128/305.5 |
| 2,457,772 | 12/1948 | Brown | 128/305.5 |
| 3,415,251 | 12/1968 | Knapp | 128/305.5 |
| 3,583,403 | 6/1971 | Pohl | 128/305.5 |
| 3,820,543 | 6/1974 | Vanjushin | 128/305.5 |
| 3,934,591 | 1/1976 | Gleason | 128/305.5 |

*Primary Examiner*—Richard J. Johnson
*Attorney, Agent, or Firm*—Wigman & Cohen

[57] ABSTRACT

A mucotome or mucous membrane cutter for mucogingival membrane surgery is disclosed. The mucotome comprises a handle having a small, compactly designed cutting head arranged on its forward end, the cutting head including a circular cylindrical blade-holding roller which is reciprocable parallel to the blade edge in a guide by means of a drive shaft having an eccentric crank pin engaging in cross grooves of the blade-holding roller. A cutting shoe is mounted to the ends of the blade-holding roller and is rotatable relative to the cutting head through a limited angle. The cutting head is also selectively positionable in at least two angular positions relative to its support. The cutting blade is secured in a longitudinal radial slot in the roller and projects therefrom through a guide slit formed in a crosspiece of the cutting shoe. The construction and arrangement of the cutting head and cutting shoe assure a compact, versatile structure having a number of adjustment possibilities.

12 Claims, 5 Drawing Figures

MUCOUS MEMBRANE CUTTER FOR MUCOGINGIVAL MEMBRANE SURGERY

BACKGROUND OF THE INVENTION

The present invention relates to a mucotome, that is, a dermatome for mucous membranes, having a handle and a cutting head arranged on its forward end, with a blade holder for carrying a cutting blade. The blade holder is reciprocable parallel to the cutting surface along an axial guide formed in the cutting head and a cutting shoe, formed as part of the cutting head, contributes to the determination of the cutting depth of the cutting blade. A drive shaft is arranged in a radial sliding support formed by the cutting head and has a front crank with an eccentric crank pin engagable in a cross groove in the blade holder, which cross groove extends in a radial plane and has a cross section that is adapted to receive the crank pin.

In a mucotome of the type known from German Utility Model Publication No. 7,526,361, which is moved by pulling, the cutting shoe is also formed as a blade holder comprising an element which is bent twice in the same direction with two generally rectangular bends. The blade holder is provided with transverse bores and is guided along two parallel rods in the cutting head. The primary disadvantage of this known mucotome is that the cutting head cannot be formed as compactly as necessary because of the guiding of the cutting shoe and blade holder along the rods when introducing and handling the mucotome in the oral cavity.

SUMMARY AND OBJECTS OF THE INVENTION

It is, therefore, a primary objective of the invention to provide a mucotome of the general type mentioned above with a cutting head which can be made very small and compact.

This object is accomplished according to the invention, in that a straight prismatic bar or a circular cylindrical roller with a longitudinally extending radial slit is provided as a blade holder to hold the razor blade-like cutting blade, and that the portion of the cutting blade that projects radially out of the receiving slit, in the case of a cylindrical roller, is guided in a slit of the cutting head.

This guiding is only necessary when the blade holder provided is the preferred circular cylindrical roller, because the non-cylindrical cross section of a prismatic bar together with the corresponding cross section of its axial guide form a means of assuring that there is no rotation of the bar. The alternative solution with roller and cutting head slit is basically known from U.S. Pat. No. 1,736,246, which discloses a dermatome of a dissimilar type. The use of a straight prismatic bar or a circular cylindrical roller as the blade holder allows a compact construction of the cutting head, without losing the percise guiding and the inexpensive drive of the blade holder. This will be clear from the exemplary embodiment described hereinafter.

In the known similar mucotome, the cutting blade has an unchangeable relative position with respect to the handle, an arrangement which has been found to be disadvangeous in practice. It is, therefore, advantageous to design and construct the mucotome according to the invention in such a manner, that this disadvantage is overcome and the cutting blade can be brought into various relative positions with respect to the handle as in the dermatome disclosed in U.S. Pat. No. 3,934,591. A partial solution exists according to one preferred embodiment of the mucotome according to the invention in that the guide slit for the cutting blade is formed in the cutting shoe, that the cutting head has a rotating joint upon which the cutting shoe is rotatably mounted, that the roller holding the blade forms the shaft of the rotating joint, that the mount of the rotating joint has a longitudinal slit through which the cutting blade projects, the azimuthal width of such slit corresponding to the maximum angle of rotation of the cutting shoe. The concentricity of this arrangement assures, in a simple manner, a first degree of freedom permitting rotation of the cutting shoe without limiting the compactness of the cutting head.

In the preferred embodiment, the cross groove in the blade holder, which receives the crank pin, consists of two straight sections that merge with each other at a rigid knee having a knee angle of at least 90°. This angle allows a maximum rotation of the cutting head of 90°, during which rotation the crank pin moves through the cross groove, which can easily be formed in the preferred embodiment to allow the crank pin sufficient play.

The preferred embodiment is distinguished by the fact that the cutting shoe has two clamping plates, which bear against the at least partially ring-shaped end surfaces of the rotational joint mount and which are provided with coaxial bores for the engagement of the ends of the blade-supporting roller which extend from each end of the mount, and a crosspiece that connects the two plates and is provided with a guide slit for the cutting blade. The two clamping plates with their bores and the connecting crosspiece with its guide slit assure an inexpensive mounting of the roller with the cutting blade in the cutting shoe. The same holds true, of course, for the mounting of the cutting shoe on the blade-supporting roller. The crank pin of the drive shaft allows only a certain, limited axial movement of the blade-supporting roller as determined by the stroke of the crankpin.

In the preferred embodiment, the two clamping plates and the connecting crosspiece are integrally formed in one piece and the guide slit extends along the entire length of the connecting crosspiece and through the two clamping plates. This embodiment is especially advantageous, because by means thereof only a minimal expense is necessary for mounting the cutting head. More specifically, all that need be done during mounting is to insert the one-piece chassis of the cutting shoe, which chassis consists of the two clamping plates and the connecting crosspiece, onto the eye-shaped rotational mount of the cutting head, until the bores in the clamping plates align with the hollow bore of the mount, whereupon the roller with the cutting blade and the mount can be inserted in an axial direction into the clamping plate bores and the guide slit respectively. Finally, the drive shaft can be inserted into the cutting head in such a manner that its crank pin engages in the cross groove of the roller. Thereafter, the crank pin holds the roller and the roller holds the cutting shoe, which, in turn, prevents relative rotational movement of the cutting blade.

In order to simplify the mounting and securing of the cutting shoe onto the rotational joint mount, the preferred embodiment is also distinguished by a clamping screw extending freely rotatably through one of the clamping plates and screwed into a suitably threaded bore of the other clamping plate. The clamping screw is arranged generally diametrically opposite the connecting crosspiece with respect to the bores in the clamping plates. By loosening the clamping screw, the cutting head can easily be pulled from the rotational joint mount after the retraction of the crank pin and the sideways removal of the roller containing the blade, if this is desired. During the mounting of the cutting head, a tightening of the clamping screw causes the clamping plates of the cutting shoe to be pressed tightly against the partial ring-shaped end surfaces of the rotational joint mount.

In the preferred embodiment, the clamping plates are formed as mirror images of each other and are approximately elliptical in shape. A grooved roller is freely rotatably mounted between the clamping plates and the cylindrical roller, the connecting crosspiece, the grooved roller and the clamping screw are arranged successively along the major axis of the elliptical clamping plates. The cutting shoe, which tightens the mucous membrane by means of the cylinder, thereby is given the desired flat shape, which simplifies the handling of the cutting head in the oral cavity. This effect is enhanced in the preferred embodiment in that the clamping plates on the end of the cutting shoe that carries the cylinder each have a skid, which operate together with the cutting edge and the cylinder and which support the cutting shoe outside the cutting area on the mucous membrane and on its rigid foundation, whereby the mucous membrane is tightened across the cutting area.

The fact that the cutting head in the preferred embodiment is detachably mounted to a support of the handle on the end opposite the cutting shoe by means of a screw cap, results not only in a simplified mounting of the mucotome, but also results in the further advantage, that the present cutting head can easily and rapidly be replaced by another cutting head with a different cutting width and/or cutting depth. It is of course, also possible to retain all of the other elements of the cutting head and replace only the cutting shoe.

Starting with the embodiment of the cutting head on the handle, a further partial solution of the problem of improving the mucotome according to the invention in such manner that the cutting blade can be adjusted to different relative angular positions with respect to the handle, exists in the possibility of an angled support such as that in the preferred embodiment, in that the rear end surface of the cutting head has at least two and preferably four depressions or slots and that a locking bolt or pin projects from the front end of the support, which locking pin engages selectively in one of the slots. Depending on the number of slots, the cutting head can be connected with the support in various rotational positions about the common axis of the drive shaft and the support, the axis of which support, as mentioned earlier, together with the main axis of the handle can form an obtuse angle when necessary or desired. Consequently, the cutting shoe which guides the cutting blade has a second degree of freedom, which can be used for its stepwise adjustment. Even when no flexible drive shaft is used, a straight, rigid drive shaft can be used, which extends from the roller holding the blade and ends at the base of the support, i.e., it penetrates the separating plane between the cutting head and the handle, which plane is bridged by the screw cap. In order to also control the drive shaft from outside the cutting head, that is, at its end opposite the cutting shoe, it is provided in the preferred embodiment, that a mounting sleeve with an outer collar which holds the drive shaft is arranged in the cutting head and in the support, and engages between the confronting end surfaces of the cutting head and the support, and has a number of openings for the passage of the locking pin that corresponds to the number and position of the slots in the rear end of the cutting head. The locking pin projects from the front end of the support, and its cross-sectional shape determines the shape of the openings. The perforated collar holds the mounting sleeve against rotation.

In view of the smallness and compactness of the mucotome according to the invention, the lubrication of the drive shaft, which rotates when placed in operation, and the pivoting roller create difficulties. These difficulties are avoided in the preferred embodiment in that the mounting sleeve is provided with longitudinal grooves on its outer side, which grooves extend through the collar, and after removal of the cutting head from the handle support are accessible from the front side. The mounting sleeve is also provided with a radial bore, which is connected with a lubricant reservoir formed by a wide annular groove in the drive shaft. From this supply reservoir, the lubricant reaches the annular chamber surrounding the mounting sleeve after passing between the drive shaft, the mounting sleeve and through the bore, from which annular chamber the lubricant reaches the rotational joint of the cutting shoe.

In the following, the invention is described in greater detail with the aid of drawings of the exemplary, preferred embodiment of the mucotome according to the invention.

DETAILED DESCRIPTION OF A PREFERRED EMBODIMENT

Figure 1:
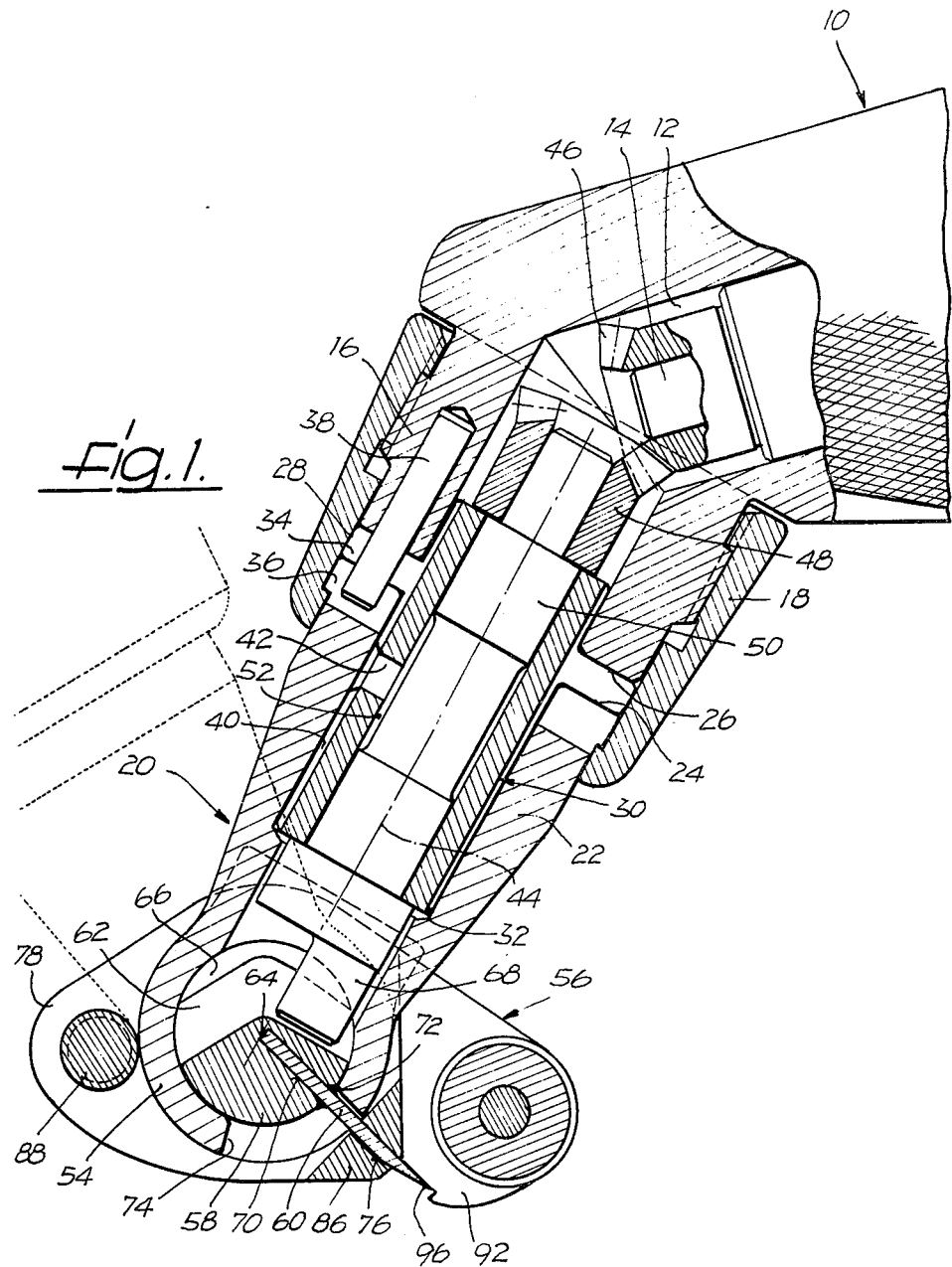
FIG. 1 is a central longitudinal section through the exemplary embodiment with a cut-away of the handle.

The exemplary embodiment has a basically straight, not completely illustrated handle 10 having a cylindrical hollow chamber 12 within which a main drive shaft 14 extends forwardly. On the forward end of the handle 10 a circular cylindrical support 16 is formed in one piece, the axis of which forms an obtuse angle of approximately 135° with the axis of the hollow chamber 12.

A cutting head 20 is detachably secured to the support 16 by means of a screw cap 18. Cutting head 20 has a hollow, somewhat blunt cone-shaped element 22, the rear annular surface 24 of which confronts the similarly annular shaped end surface 26 of the support 16 at a certain spacing. Interposed in the space between surfaces 24, 26 is an outer collar 28 of a mounting sleeve 30. On one side of the collar 28, the mounting sleeve 30 extends into the support 16 and, on the other side of the collar, extends into a cylindrical hollow chamber 32 of the cone-shaped cutting head element 22. The outer collar 28 and the rear surface 24 of the cutting head element 22 have, at the same positions, four equi-angularly spaced radial slots 34, 36, respectively, about their peripheries, the latter slots 36 interrupting the surface 24. A locking bolt or pin 38 is engaged in one pair of coincident slots 34 and 36 which has a diameter adapted to the width of the slot and is anchored in the support 16. The mounting sleeve 30 has a radial bore 42 and, on its outer surface, longitudinal grooves 40 extending through the collar 28.

On the forward end of the main drive shaft 14 there is rigidly supported a forwardly toothed bevel gear 46, which meshes with a similar bevel gear 48 rigidly mounted on the rear end of a drive shaft 50, which, in turn, is mounted in the sleeve 30. Drive shaft 50 has a wide annular groove 52 communicating with and adjacent the radial bore 42 in the sleeve 30.

An eye-like, circular cylindrical rotational joint mount 54 is formed on the lower end of the cutting head element 22, the hollow space of which rotational joint mount 54 intersects the hollow space 32 of the cutting head element 22, which space 32 has a somewhat smaller cross-sectional area at the lower end of the mounting sleeve 30. The shaft of the rotational joint, by means of which a cutting shoe 56 is joined as a further portion of the cutting head 20 at its stationary element 22, comprises a circular cylindrical roller 58, which carries a cutting blade 60. The roller 58 has a milled-out cross groove 62 which is formed outside the roller axis and comprises two straight sections that form a rigid knee having an angle of about 120°. The groove 62 is also provided with two chamfers 66, one on either side thereof. The crank pin 68 of a crank on the forward end of the drive shaft 50 engages in the cross groove 62 and extends almost to the bottom of the groove. The diameter of the crank pin 68 is the same as the width of the cross groove 62 and is only slightly smaller than the length of each of the straight sections of the cross groove.

The roller 58, which, when moving, pivots about its axis 64, has a longitudinally extending radial receiving slit 70 in which the cutting blade 60 is mounted. The cutting blade 60 is secured to the roller 58 at the location of its radial slit 70 by solder 72 on both sides of the slit. The portion of the cutting blade 60 that projects out of the receiving slit 70 passes through a continuous, longitudinal slit 74 in the rotational joint mount 54. The dimensions of slit 74 correspond to the desired maximum angle of rotation of the cutting shoe 56. The cutting blade 60 is mounted in a guide slit 76 of the cutting shoe 56. The guide plane that coincides with the plane of the flat cutting blade 60 contains the roller axis 64 which intersects the axis 44 of the drive shaft 50 at right angles.

Figure 2:
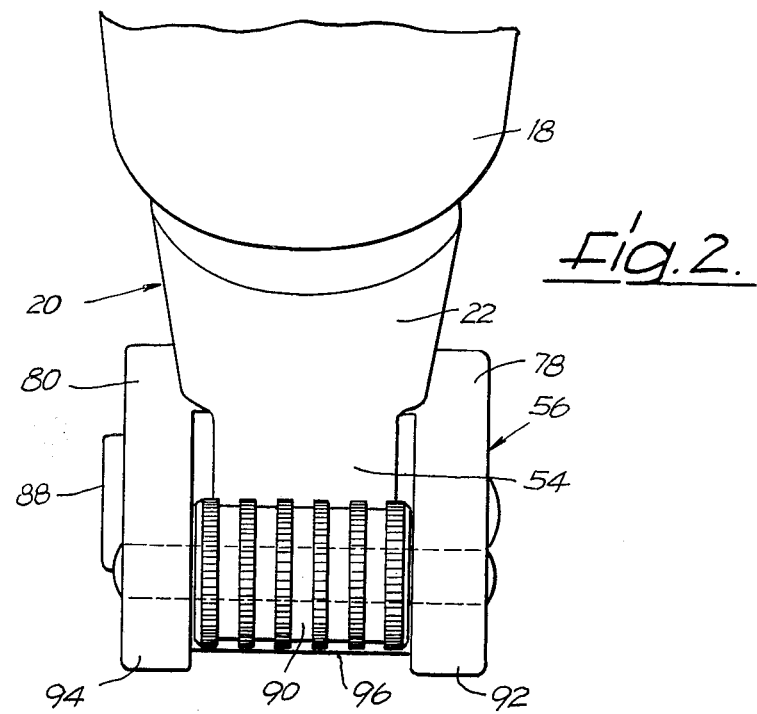
FIGS. 2 and 3 are views of the cutting head of the exemplary embodiment from opposite directions.
Figure 3:
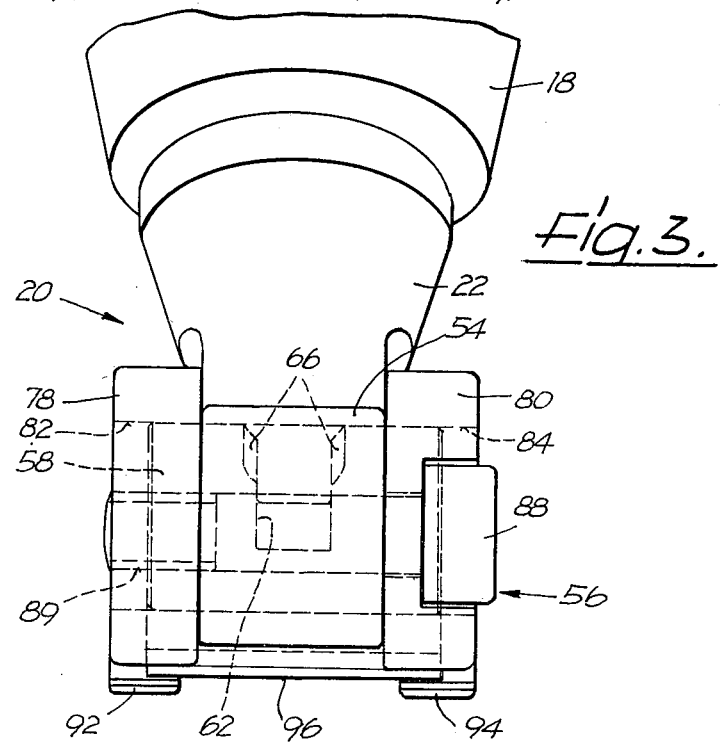

As may be best seen in FIGS. 2 and 3, the cutting shoe 56, which has limited rotation about the roller axis 64, has two clamping plates 78 and 80 which bear against the oppositely disposed, partially ring-shaped end surfaces of the rotational joint mount 54. The clamping plates 78 and 80 are mirror images of each other, are formed approximately elliptically, and are provided with coaxial bores 82 and 84, respectively, for the engagement of the ends of the roller 58 that project outwardly from each end of the mount 54. The two plates 78 and 80 are connected by means of a crosspiece 86, which is integrally formed in one piece with the plates 78, 80. The guide slit 76 for the cutting blade 60 is disposed in this crosspiece 86, and the cutting blade 60 extends through the connecting crosspiece 86 over the entire length thereof between the two clamping plates 78, 80 and projects, with its cutting edge 96 into the space beyond the crosspiece 86. A clamping screw 88 extends freely rotatably through one of the clamping plates, namely, the plate 80 and this screw 88 is screwed into a suitably threaded bore 89 in the other clamping plate 78. The crosspiece 86 is arranged generally diametrically with respect to the bores 82 and 84 in the clamping plates. A grooved cylinder 90 is also mounted between the two clamping plates 78 and 80 in such manner as to be freely rotatable, and in such position that the cylinder 90, the crosspiece 86, the roller 58 and the clamping screw 88 are arranged successively generally along the major axis of the elliptically-shaped clamping plates. Finally, each of the clamping plates 78, 80 have, on the end of the cutting shoe 56 that carries the cylinder 90, a guide skid 92, 94, respectively, between which the cutting edge 96 of the cutting blade 60 extends.

Figure 4:
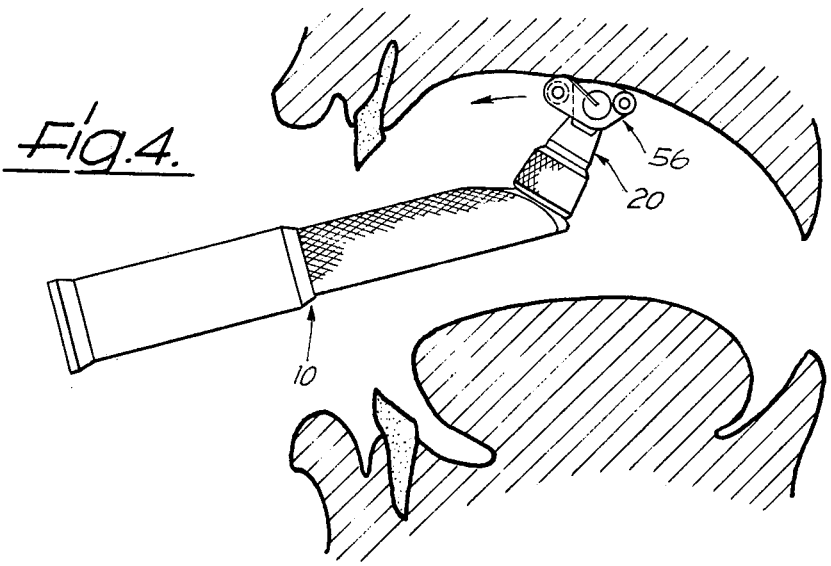
FIGS. 4 and 5 show the manner of use of the mucotome in the oral cavity for cutting in opposite directions.
Figure 5:
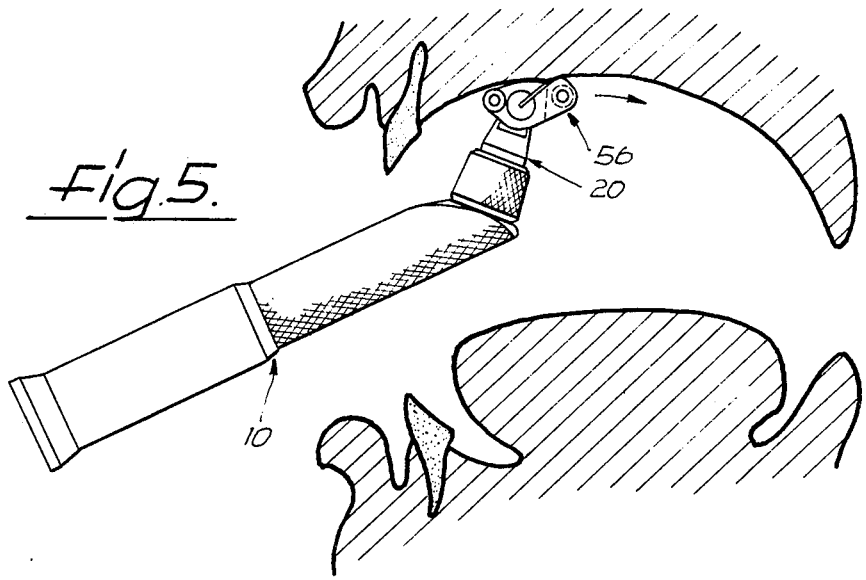

From the FIGS. 4 and 5 it is apparent that the mucotome according to the invention, in the embodiment described above, can be moved either by pushing or pulling without changing the relative angular position of the cutting head 20 with regard to the handle 10, depending on the angular position of the cutting shoe 56. The surgeon can also change the mentioned relative angular position, exchange the cutting head 20 and replace the handle 10 with a different one having a support that carries the cutting head angled to a greater or lesser degree, such as 30° instead of 45°. It is also possible to provide a support which orients the handle 10 and cutting head 20 coaxially.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. In a mucotome having a handle and a cutting head arranged at one end of the handle, said cutting head including a blade holder carrying a cutting blade with a cutting edge and a cutting shoe for determining the cutting depth of the blade, said cutting head having a guide for the blade holder along which the blade holder is reciprocally movable parallel to the cutting edge of the cutting blade by means of a rotatable drive shaft having an eccentric crank pin engageable in a cross groove in the blade holder, the improvement comprising said blade holder comprising a circular cylindrical blade-holding roller having a longitudinally extending radial slit for receiving the cutting blade, said cutting blade projecting out of said radial slit, said cutting head having a guide slit through which said cutting blade projects, said cutting head being pivotable about the longitudinal axis of the circular cylindrical blade-holding roller, whereby the cutting blade may be reoriented to cut in the opposite direction.

2. The improvement according to claim 1, wherein said handle includes a cutting head support, said cutting head being detachably secured to said support by a screw cap.

3. In a mucotome having a handle and a cutting head arranged at one end of the handle, said cutting head including a blade holder carrying a cutting blade with a cutting edge and a cutting shoe for determining the cutting depth of the blade, said cutting head having a guide for the blade holder along which the blade holder is reciprocally movable parallel to the cutting edge of the cutting blade by means of a rotatable drive shaft having an eccentric crank pin engageable in a cross groove in the blade holder, the improvement comprising said blade holder comprising a circular cylindrical blade-holding roller having a longitudinally extending radial slit for receiving the cutting blade, said cutting blade projecting out of said radial slit, said cutting head having a guide slit through which said cutting blade projects, wherein said guide slit is arranged in the cutting shoe, the cross groove in the blade-holding roller having a generally semicircular locus, the center point of which lies on the axis of the roller, said cutting head guide comprising a rotational joint mount having a generally cylindrical tubular portion in which said roller is guided, said cutting shoe being rotatably mounted to said rotational joint mount for limited angular rotation through a given angle, said tubular portion having a longitudinal slot in a wall thereof through which said blade extends, the arcuate extent of said slot corresponding to said given angle.

4. In a mucotome having a handle and a cutting head arranged at one end of the handle, said cutting head including a blade holder carrying a cutting blade with a cutting edge and a cutting shoe for determining the cutting depth of the blade, said cutting head having a guide for the blade holder along which the blade holder is reciprocally movable parallel to the cutting edge of the cutting blade by means of a rotatable drive shaft having an eccentric crank pin engageable in a cross groove in the blade holder, the improvement comprising said blade holder comprising a circular cylindrical blade-holding roller having a longitudinally extending radial slit for receiving the cutting blade, said cutting blade projecting out of said radial slit, said cutting head having a guide slit through which said cutting blade projects, wherein said guide slit being arranged in the cutting shoe, the cross groove in the blade-holding roller having a generally semicircular locus, the center point of which lies on the axis of the roller, said cutting head guide comprising a rotational joint mount having a generally cylindrical tubular portion in which said roller is guided, said cutting shoe being rotatably mounted to said rotational joint mount for limited angular rotation through a given angle, said tubular portion having a longitudinal slot in a wall thereof through which said blade extends, the arcuate extent of said slot corresponding to said given angle, wherein said cross groove comprises two intersecting grooves formed transversely of said roller, said two grooves defining a rigid knee having an angle of at least 90°.

5. In a mucotome having a handle and a cutting head arranged at one end of the handle, said cutting head including a blade holder carrying a cutting blade with a cutting edge and a cutting shoe for determining the cutting depth of the blade, said cutting head having a guide for the blade holder along which the blade holder is reciprocally movable parallel to the cutting edge of the cutting blade by means of a rotatable drive shaft having an eccentric crank pin engageable in a cross groove in the blade holder, the improvement comprising said blade holder comprising a circular cylindrical blade-holding roller having a longitudinally extending radial slit for receiving the cutting blade, said cutting blade projecting out of said radial slit, said cutting head having a guide slit through which said cutting blade projects, wherein said guide slit being arranged in the cutting shoe, the cross groove in the blade-holding roller having a generally semicircular locus, the center point of which lies on the axis of the roller, said cutting head guide comprising a rotational joint mount having a generally cylindrical tubular portion in which said roller is guided, said cutting shoe being rotatably mounted to said rotational joint mount for limited angular rotation through a given angle, said tubular portion having a longitudinal slot in a wall thereof through which said blade extends, the arcuate extent of said slot corresponding to said given angle, wherein said rotational joint mount has oppositely disposed partially ring-shaped end surfaces, said cutting shoe including a pair of clamping plates, one each of which is arranged to bear against a respective end surface of the rotational joint mount, each of said clamping plates having a bore for engaging a respective end of the blade-holding roller, a crosspiece connecting said clamping plates, the guide slit for the cutting blade being formed in said crosspiece.

6. The improvement according to claim 5, wherein said clamping plates and connecting crosspiece are integrally formed in one piece, said guide slit extending entirely through the longitudinal extent of said crosspiece between said clamping plates and through said clamping plates.

7. The improvement according to claim 5, including a clamping screw extending freely rotatably through one of said clamping plates and threadably engaging in a threaded bore in the other clamping plate, said connecting crosspiece and said clamping screw being arranged generally diametrically to and on opposite sides of said roller-engaging bores in the clamping plates.

8. The improvement according to claim 7, wherein said clamping plates are substantially elliptically shaped mirror images of each other and including a grooved cylinder rotatably mounted between the clamping plates, said grooved cylinder, said connecting crosspiece, said blade-holding roller and said clamping screw being successively arranged generally along the major axis of the elliptically-shaped clamping plates.

9. The improvement according to claim 8, wherein each of said clamping plates is provided with a guide skid arranged adjacent the grooved cylinder and cooperating with said cylinder during a cutting operation.

10. In a mucotome having a handle and a cutting head arranged at one end of the handle, said cutting head including a blade holder carrying a cutting blade with a cutting edge and a cutting shoe for determining the cutting depth of the blade, said cutting head having a guide for the blade holder along which the blade holder is reciprocably movable parallel to the cutting edge of the cutting blade by means of a rotatable drive shaft having an eccentric crank pin engageable in a cross groove in the blade holder, the improvement comprising said blade holder comprising a circular cylindrical blade-holding roller having a longitudinally extending radial slit for receiving the cutting blade, said cutting blade projecting out of said radial slit, said cutting head having a guide slit through which said cutting blade projects, said handle including a cutting head support, said cutting head being detachably secured to said support by a screw cap, and wherein the axis of said support lies at an angle with respect to the axis of said handle, said cutting head including an end surface having at least two angularly spaced slots therein and confronting an end surface of the support, a locking pin projecting from the end surface of said support, said locking pin being selectively engageable in one of the slots in the end surface of said cutting head.

11. The improvement according to claim 10, including a mounting sleeve having an outer annular collar and arranged in said cutting head and said cutting head support, said sleeve housing said drive shaft, said outer collar engaging between the confronting end surfaces of said cutting head and said cutting head support, said outer collar having openings therethrough corresponding to the number and location of the slots in the end surface of said cutting head.

12. The improvement according to claim 11, wherein said mounting sleeve is provided on its outer surface with longitudinal grooves extending through said outer collar and a radial bore, said drive shaft having an annular groove therearound defining a lubricant reservoir, said radial bore communicating with said annular groove of the drive shaft.

* * * * *

UNITED STATES PATENT AND TRADEMARK OFFICE
CERTIFICATE OF CORRECTION

PATENT NO. : 4,211,232
DATED : July 8, 1980
INVENTOR(S) : Werner Mörmann, Gerhard Bofinger, Wilfried Wölfle It is certified that error appears in the above-identified patent and that said Letters Patent are hereby corrected as shown below:

On the title page, left column, item [75], line 4, change "Wölfie" to --Wölfle--; item [73], line 1, change "Werker" to --Werke--.

Signed and Sealed this

*Fourth* Day of *November 1980*

[SEAL]

*Attest:*

SIDNEY A. DIAMOND

*Attesting Officer*  *Commissioner of Patents and Trademarks*